(12) United States Patent
Downie et al.

(10) Patent No.: US 12,124,113 B2
(45) Date of Patent: Oct. 22, 2024

(54) IDENTIFICATION OF CONTACT LENS WEARERS PREDISPOSED TO CONTACT LENS DISCOMFORT

(71) Applicants: CooperVision International Limited, Fareham (GB); The University of Melbourne, Victoria (AU)

(72) Inventors: Laura Elizabeth Downie, Melbourne (AU); David Charles Jackson, Balwyn North (AU); Algis Jonas Vingrys, Melbourne (AU); Nancy J. Keir, Pleasanton, CA (US); Inna Maltseva, San Francisco, CA (US)

(73) Assignee: COOPERVISION INTERNATIONAL LIMITED, Fareham (GB)

( * ) Notice: Subject to any disclaimer, the term of this patent is extended or adjusted under 35 U.S.C. 154(b) by 0 days.

(21) Appl. No.: 18/114,287

(22) Filed: Feb. 27, 2023

(65) Prior Publication Data
US 2023/0244091 A1      Aug. 3, 2023

Related U.S. Application Data

(62) Division of application No. 16/286,637, filed on Feb. 27, 2019, now Pat. No. 11,619,832.
(Continued)

(51) Int. Cl.
*G02C 7/04*      (2006.01)
*C07K 16/24*     (2006.01)
(Continued)

(52) U.S. Cl.
CPC ............ *G02C 7/047* (2013.01); *C07K 16/244* (2013.01); *G01N 33/6869* (2013.01);
(Continued)

(58) Field of Classification Search
CPC ........ G02C 7/047; G02C 7/027; G02C 7/049; C07K 16/244; G01N 33/6869;
(Continued)

(56) References Cited

U.S. PATENT DOCUMENTS

| 7,723,124 B2 | 5/2010 | Aberl et al. |
| 2011/0027290 A1 | 2/2011 | Allan et al. |

(Continued)

FOREIGN PATENT DOCUMENTS

| CN | 104231080 A | 12/2014 |
| CN | 106950364 A | 7/2017 |

(Continued)

OTHER PUBLICATIONS

International Search Report and Written Opinion issued in corresponding International Patent Application No. PCT/GB2019/050624 dated May 10, 2019 (17 pages).
(Continued)

*Primary Examiner* — James C. Jones
(74) *Attorney, Agent, or Firm* — Kilyk & Bowersox, P.L.L.C.

(57) ABSTRACT

Methods and devices to identify contact lens wearers predisposed to contact lens discomfort are described. The methods and devices involve obtaining a tear film sample from a person and determining an amount of interleukin-17A present in the tear film sample.

4 Claims, 1 Drawing Sheet

Related U.S. Application Data (60) Provisional application No. 62/640,091, filed on Mar. 8, 2018.

(51) Int. Cl.
  *G01N 33/68* (2006.01)
  *G02C 7/02* (2006.01)
(52) U.S. Cl.
  CPC .............. *G02C 7/027* (2013.01); *G02C 7/049* (2013.01); *G01N 2333/54* (2013.01); *G01N 2800/16* (2013.01)
(58) Field of Classification Search
  CPC ........... G01N 2333/54; G01N 2800/16; G01N 33/523; G01N 33/5302; G01N 33/54386; G01N 33/558
  See application file for complete search history.

(56) References Cited

U.S. PATENT DOCUMENTS

| | | | |
|---|---|---|---|
| 2014/0314798 A1 | 10/2014 | Pflugfelder et al. | |
| 2019/0278105 A1 | 9/2019 | Downie et al. | |

FOREIGN PATENT DOCUMENTS

| | | | | |
|---|---|---|---|---|
| WO | 9518826 A2 | 7/1995 | | |
| WO | 2012018767 A2 | 2/2012 | | |
| WO | 2013016124 A1 | 1/2013 | | |
| WO | 2013037970 A1 | 3/2013 | | |
| WO | WO-2013059644 A1 * | 4/2013 | ............. | C12Q 1/686 |
| WO | 2013098419 A1 | 7/2013 | | |
| WO | 2015069927 A1 | 5/2015 | | |
| WO | 2017116826 A1 | 7/2017 | | |

OTHER PUBLICATIONS

Search Report issued in corresponding United Kingdom Patent Application No. GB1902987.5 dated May 14, 2019 (4 pages).
Acera et al., "Inflammatory Markers in the Tears of Patients with Ocular Surface Disease," Ophthalmic Research, 2008, 40(6), pp. 315-321.
Acera et al., "Tear MMP-9 Levels as a Marker of Ocular Surface Inflammation in Conjunctivochalasis," Investigative Ophthalmology & Visual Science, 2013, 54(13), pp. 8285-8291.
Aluri et al., "Role of Matrix Metalloproteinases 2 and 9 in Lacrimal Gland Disease in Animal Models of Sjogren's Syndrome," Investigative Ophthalmology & Visual Science, 2015, 56(9), pp. 5218-5228.
Bullimore et al., "The Risk of Microbial Keratitis With Overnight Corneal Reshaping Lenses," Optometry and Vision Science, 2013, 90(9), pp. 1-8.
Chalmers et al., "Contact Lens Dry Eye Questionnaire-8 (CLDEQ-8) and Opinion of Contact Lens Performance," Optometry and Vision Science, 2012, 89(10), pp. 1435-1442.
Dogan et al., "Corneal confocal microscopy and dry eye findings in contact lens discomfort patients," Contact Lens and Anterior Eye, 2018, vol. 41, No. 1, pp. 101-104.
Dogru et al., "The effects of 2 week senofilcon—A silicone hydrogel contact lens daily wear on tear functions and ocular surface health status," Contact Lens & Anterior Eye, 2011, 34(2), pp. 77-82.
Dumbleton et al., "The Impact of Contemporary Contact Lenses on Contact Lens Discontinuation," Eye & Contact Lens, 2013, 39(1), pp. 93-99.
Efron, N., "Contact lens wear is intrinsically inflammatory," Clinical and Experimental Optometry, 2016, 100(1), pp. 1-17.
Epstein et al., "HLA-DR Expression as a Biomarker of Inflammation for Multicenter Clinical Trials of Ocular Surface Disease," Exp Eye Res., 2013, 111, pp. 1-24.
Gad et al., "Tear film inflammatory cytokine upregulation in contact lens discomfort," The Ocular Surface, 2019, vol. 17, pp. 89-97.

Gao et al., "ICAM-1 expression predisposes ocular tissues to immune-based inflammation in dry eye patients and Sjogrens syndrome-like MRL/lpr mice," Experimental Eye Research, 2004, 78(4), pp. 823-835.
Jackson et al., "Tear Interferon-Gamma as a Biomarker for Evaporative Dry Eye Disease," Investigative Ophthalmology & Visual Science, 2016, 57(11), pp. 4824-4830.
Jung et al., "Tear Cytokines as Biomarkers for Chronic Graft-versus-Host Disease," Biology of Blood Marrow Transplantation, 2015, 21(12), pp. 2079-2085.
Kang et al., "Interleukin-17 in Various Ocular Surface Inflammatory Diseases," Journal of Korean Medical Science, 2011, vol. 26, No. 7, pp. 938-944.
Lanza et al., "The Matrix Metalloproteinase 9 Point-of-Care Test in Dry Eye," Ocul Surf., 2016, 14(2), pp. 1-14.
Lemp et al., "The Definition and Classification of Dry Eye Disease: Report of the Definition and Classification Subcommittee of the International Dry Eye WorkShop (2007)," DEWS Definition and Classification Subcommittee, The Ocular Surface, 2007, 5(2), pp. 75-92.
Levi-Montalcini et al., "Nerve growth factor: from neurotrophin to neurokine," TINS, 1996, 19(11), pp. 514-520.
Liu et al., "Elevated Nerve Growth Factor in Dry Eye Associated With Established Contact Lens Wear," Eye & Contact Lens, 2009, 35(5), pp. 232-237.
Liu et al., "Analysis of Th17-associated cytokines and clinical correlations in patients with dry eye disease," PLoS One, 2017, vol. 12(4):e0173301, pp. 1-12.
Lopez-De La Rosa et al., "Corneal Sensitivity and Inflammatory Biomarkers in Contact Lens Discomfort," Optometry and Vision Science, 2015, 93, pp. 1-9.
Masoudi et al., "Contact Lens-Induced Discomfort and Protein Changes in Tears," Optometry and Vision Science, 2016, 93(8), pp. 1-8.
Massingale et al., "Analysis of Inflammatory Cytokines in the Tears of Dry Eye Patients," Cornea, 2009, 28(9), pp. 1023-1027.
Moschos et al., "Increased Eotaxin in Tears of Patients Wearing Contact Lenses," Cornea, 2004, 23(8), pp. 771-775.
Nichols et al., "The TFOS International Workshop on Contact Lens Discomfort: Executive Summary," Investigative Ophthalmology & Visual Science, 2013, 54(11), pp. TFOS7-TFOS13.
Poyraz et al., "Elevated Tear Interleukin-6 and Interleukin-8 Levels Associated With Silicone Hydrogel and Conventional Hydrogel Contact Lens Wear," Eye & Contact Lens, 2012, 38(3), pp. 146-149.
Robciuc et al., "Lipid-Modifying Enzymes in Human Tear Fluid and Corneal Epithelial Stress Response," Investigative Ophthalmology & Visual Science, 2014, 55(1), pp. 16-24.
Schaumberg et al., Development and Validation of a Short Global Dry Eye Symptom Index, The Ocular Surface, 2007, 5(1), pp. 50-57.
Schiffman et al., "Reliability and Validity of the Ocular Surface Disease Index," Arch Ophthalmol., 2000, 118(5), pp. 615-621.
Schultz et al., "Interleukin-6 Levels in Tears of Contact Lens Wearers," Journal of Interferon and Cytokine Research, 2000, 20(3), pp. 309-310.
Thakur et al., "Contact Lens Wear Alters the Production of Certain Inflammatory Mediators in Tears," Exp. Eye Res., 2000, 70(3), pp. 255-259.
Validad et al., "The Study of Interleukin-17 Level in Vernal Keratoconjunctivitis Disease and its Relationship between Symptom and Sign Severity," Seminars in Ophthalmology, 2017, 32(6), pp. 721-724.
Willcox et al., "Cytokine changes in tears and relationship to contact lens discomfort," Molecular Vision, 2015, 21, pp. 293-305.
Willcox, M., "Is There a Role for Inflammation in Contact Lens Discomfort?," Eye & Contact Lens, 2017, 43(1), pp. 5-16.
Office Action issued in corresponding Taiwan Patent Application No. 108107720 dated Oct. 6, 2022 (English translation only)(6 pages).
Search Report issued in corresponding United Kingdom Patent Application No. GB1902987.5 dated Sep. 19, 2019 (3 pages).
Examination Report issued in corresponding United Kingdom Patent Application No. GB1902987.5 dated Aug. 26, 2021 (4 pages).

(56) References Cited

OTHER PUBLICATIONS

Anfossi et al., "Multiplex Lateral Flow Immunoassay: An Overview of Strategies towards High-throughput Point-of-Need Testing," Biosensors, 2019, vol. 9, No. 2 (14 pages).

* cited by examiner

IDENTIFICATION OF CONTACT LENS WEARERS PREDISPOSED TO CONTACT LENS DISCOMFORT

This application is a divisional of U.S. patent application Ser. No. 16/286,637 filed Feb. 27, 2019, which in turn claims the benefit under 35 U.S.C. § 119(e) of prior U.S. Provisional Patent Application No. 62/640,091, filed Mar. 8, 2018, which is incorporated in its entirety by reference herein.

FIELD

The field of the invention relates to methods and devices for identifying contact lens wearers predisposed to contact lens discomfort.

BACKGROUND

Inflammation is a complex non-specific tissue response elicited by exposure to potentially harmful stimuli, and is a feature of several ocular surface conditions, including dry eye disease,[1,2] conjunctivochalasis,[3] ocular allergy[4,5] and blepharitis.[4] In these clinical presentations, the anterior eye response typically features classic signs of inflammation, including redness, pain, swelling, heat and loss of normal function. These clinical signs are accompanied by alterations to the expression of inflammatory biomarkers, such as human leukocyte antigen (HLA-DR)[6] and intercellular adhesion molecule-1 (ICAM-1),[7] on ocular surface cells. Furthermore, there are changes to a tear film composition, including an upregulation of pro-inflammatory cytokines,[1,8,9] alterations to tear lipid mediators[10] and increased tear protease activity (e.g., metalloproteinases, MMP-9,[3,4,11] and MMP-2[12]).

Although uncomplicated contact lens wear is not associated with these classic signs of inflammation, the contribution of inflammation to the discomfort response experienced by some contact lens wearers remains controversial. Contact lens discomfort is a multi-factorial condition "characterized by episodic or persistent adverse ocular sensations related to contact lens wear."[23] In the United States of America, approximately three million people, or one in six contact lens wearers, abandon contact lenses annually; discomfort is the primary reason for discontinuation.[24] At present, the etiology of this discomfort response is unclear. Notably, symptoms reported by patients experiencing symptomatic lens wear (e.g., eye irritation, burning, stinging and pain) are highly similar to the symptomatology associated with dry eye disease, which is recognized to involve an inflammatory overlay.[25]

Some clinical data lend support to the presence of a low grade, sub-clinical anterior eye inflammatory response during contact lens wear that may be exaggerated in people who experience discomfort.[26] Contact lens wear alters the relative levels of a range of tear film mediators.[27-31] However, in contrast to dry eye disease where levels of tear pro-inflammatory cytokines are elevated, and also implicated in the disease process,[1,2] a link between ocular discomfort and the upregulation of specific inflammatory mediators has not been clearly demonstrated.[32,33] Changes to key tear film mediators, including the complement cascade, kinin cascade and histamine, do not appear to be associated with comfort levels.[34] Roles for neurokine growth factor, which can induce hyperalgesia and mast cell degranulation,[35] and the prolactin-induced protein, which modulates water transport in the lacrimal gland,[36] have been proposed.[37] Other potential molecular candidates include degraded lipids, leukotriene-B4 and peroxidation products, and the enzyme, secretory phospholipase-A2.[34]

It would be desirable identify contact lens wearers or prospective contact lens wearers who may be predisposed to developing contact lens discomfort so that proactive steps may be taken to improve the contact lens-wearing experience of these patients.

Background reference citations are appended at the end of this disclosure. Additional background references include US Publ. No. 2014/0314798, U.S. Pat. No. 7,723,124, and WO 2017/116826.

SUMMARY

As disclosed herein, the present invention is based upon the discovery that contact lens wearers or prospective contact lens wearers can be distinguished based on the amount of interleukin-17A (IL-17A) present in the wearers' tear film. With this discovery, and the present methods and devices disclosed herein, it is possible to improve contact lens products by enabling vision correction solutions that are tailored to symptomatic contact lens wearers or asymptomatic contact lens wearers, for example.

In one aspect, the invention provides a method of determining a predisposition to symptomatic contact lens wear in a patient. The method includes a step of delivering a stimulus to sensory neurons of a cornea of the patient to produce a stimulated tear sample in the patient. In the method, the concentration of IL-17A in the stimulated tear sample is determined. The method may also include an optional step of a determining a baseline concentration of IL-17A in a non-stimulated tear sample of the patient. The patient is then classified as being predisposed to symptomatic contact lens wear if (i) the concentration of IL-17A in the stimulated tear sample is at or above a cut-off value predetermined to be associated with a predisposition to symptomatic contact lens wear, and/or (ii) the concentration of IL-17A in the stimulated tear sample is higher than the baseline concentration of IL-17A.

In another aspect, the invention provides a method of determining a predisposition to asymptomatic contact lens wearer in a patient. This method includes a step of determining a baseline concentration of IL-17A in a non-stimulated tear sample of the patient. The method includes additional steps of delivering a stimulus to sensory neurons of a cornea of the patient to produce a stimulated tear sample in the patient, and determining a concentration of IL-17A in the stimulated tear sample. The patient is classified as predisposed to being an asymptomatic contact lens wearer if the concentration of IL-17A in the stimulated tear sample is less than 150% of the baseline concentration of IL-17A.

In another aspect of the invention, kits are provided.

For example, a kit for determining a predisposition for symptomatic contact lens wear in a patient includes an antibody that specifically binds to IL-17A. With such a kit, a high risk of symptomatic contact lens wear is determined using the kit if the concentration of IL-17A in a stimulated tear sample of the patient is higher than a cut-off value predetermined to be associated with symptomatic contact lens wear.

As another example, a kit for determining a predisposition for asymptomatic contact lens wear in a patient includes an antibody that specifically binds to IL-17A. With this kit, a predisposition for asymptomatic contact lens wear is determined using the kit if the concentration of IL-17A in a stimulated tear sample of the patient is lower than the concentration of IL-17A in a non-stimulated tear sample of the patient.

In another aspect, the invention provides the use of an antibody that specifically binds IL-17A in the manufacture of a device for the diagnosis of predisposition to symptomatic contact lens wear in a patient.

Additional aspects and embodiments of the present methods and devices will be apparent from the following description, examples, drawings, and claims. As can be appreciated from the foregoing and following description, each and every feature described herein, and each and every combination of two or more of such features, is included within the scope of the present invention provided that the features included in such a combination are not mutually inconsistent. In addition, any feature or combination of features may be specifically excluded from any embodiment of the present invention.

DETAILED DESCRIPTION

An immunological and clinical characterization of the ocular inflammatory response in symptomatic soft contact lens wearers compared to asymptomatic wearers was undertaken in an effort to gain insight into the nature of the inflammatory response occurring in people experiencing contact lens discomfort. This work has led to the present invention directed to methods, devices, and kits that addresses a need that exists to improve the contact lens wearing experience of patients who may be predisposed to contact lens discomfort. Disclosed herein are methods, devices, and kits for determining a predisposition to symptomatic contact lens wear in a patient. Symptomatic contact lens wear is generally characterized by the lens wearer experiencing discomfort when the lenses have been worn for 3 or more continuous hours. In one method, a tear sample is collected from a patient whose cornea and/or conjunctiva have not been subjected to any significant mechanical stimuli for a period of time, such as for example at least 30 minutes, 1 hour, 2 hours, or 4 hours prior to collection of the sample. In some methods, the patient has not worn a contact lens or has not been subjected to any other significant mechanical stimuli for at least 12 hours or 16 hours prior to collection of the sample. Throughout this disclosure, when a series of numerical values is presented with a qualifier preceding the first value, the qualifier is intended to implicitly precede each value in the series unless context dictates otherwise. Thus for example, in the above time listings, the qualifier "at least" implicitly precedes each specified time period. For simplicity, as used herein, references to "the eye" refer to the cornea and/or conjunctiva unless otherwise indicated. The collected tear sample is referred to herein as the "non-stimulated tear sample." Before or after collection of the non-stimulated tear sample, a significant mechanical stimulus is delivered to the patient's eye and a "stimulated tear sample" is collected. The concentration of interleukin-17A (IL-17A) is determined in each of the tear samples, and the patient is identified as being predisposed to symptomatic contact lens wear if the concentration of IL-17A in the stimulated tear sample is higher than the concentration of IL-17A in the non-stimulated tear sample, which is referred to herein as the "baseline concentration" of IL-17A.

In a modification to the above-described method, collection of the non-stimulated tear sample is optional. The patient is identified as being predisposed to symptomatic contact lens wear if the concentration of IL-17A in the stimulated tear sample is at or above a cut-off value predetermined to be associated with a predisposition to symptomatic contact lens wear. These methods for determining a predisposition to symptomatic contact lens wear in a patient are described in more detail below. In some examples, a non-stimulated tear sample is collected and the patient is identified as being predisposed to symptomatic contact lens wear if the concentration of IL-17A in the stimulated tear sample is both: 1) at or above a cut-off value predetermined to be associated with a predisposition to symptomatic contact lens wear, and 2) higher than the baseline concentration of IL-17A.

Also disclosed herein is a method of determining a predisposition to asymptomatic contact lens wear in a patient. Asymptomatic contact lens wear is generally characterized by the lens wearer experiencing little to no discomfort after wearing contact lenses for at least 8 continuous hours. The method comprises collecting both stimulated and non-stimulated tear samples from the patient as described above and as described in more detail below. The concentration of IL-17A in each of the tear samples is determined and the patient is identified as predisposed to asymptomatic contact lens wear if the concentration of IL-17A in the stimulated tear sample is less than the baseline concentration of IL-17A or less than a certain percentage of the baseline concentration of IL-17A. For example, the patient may be identified as predisposed to asymptomatic contact lens wear if the concentration of IL-17A in the stimulated tear sample is less than 200% or less than 150% of the baseline concentration of IL-17A.

Further disclosed herein is a method for selecting a treatment for a patient in need of vision correction, wherein the method includes optionally determining a baseline concentration of interleukin-17A (IL-17A) in a non-stimulated tear sample of the patient; delivering a stimulus to sensory neurons of a cornea of the patient to produce a stimulated tear sample in the patient; collecting the stimulated tear sample; determining a concentration of IL-17A in the stimulated tear sample; and prescribing the patient a treatment for preventing or reducing discomfort associated with contact lens wear when the concentration of IL-17A in the stimulated tear sample is at or above a cut-off value predetermined to be associated with a predisposition to symptomatic contact lens wear, and/or the concentration of IL-17A in the stimulated tear sample is higher than the baseline concentration of IL-17A.

Also disclosed herein is a method for treating a patient in need of vision correction, where the method includes optionally determining a baseline concentration of interleukin-17A (IL-17A) in a non-stimulated tear sample of the patient; delivering a stimulus to sensory neurons of a cornea of the patient to produce a stimulated tear sample in the patient; collecting the stimulated tear sample; determining a concentration of IL-17A in the stimulated tear sample and whether the concentration is at or above a cut-off value predetermined to be associated with a predisposition to symptomatic contact lens wear, and/or whether the concentration of IL-17A in the stimulated tear sample is higher than the baseline concentration of IL-17A, and if so, then providing prescribed contact lenses to the patient for the vision correction and administering a neuropathic agent, an anti-inflammatory agent, a wetting eye drop, or any combinations thereof or providing prescribed spectacle lenses to the patient for the vision correction.

Further disclosed is a method for treating a patient in need of vision correction, where the method includes optionally determining a baseline concentration of interleukin-17A (IL-17A) in a non-stimulated tear sample of the patient; delivering a stimulus to sensory neurons of a cornea of the patient to produce a stimulated tear sample in the patient; collecting the stimulated tear sample; determining a concentration of IL-17A in the stimulated tear sample; and providing a prescription to the patient for treatment for preventing or reducing discomfort associated with contact lens wear when the concentration of IL-17A in the stimulated tear sample is at or above a cut-off value predetermined to be associated with a predisposition to symptomatic contact lens wear, and/or the concentration of IL-17A in the stimulated tear sample is higher than the baseline concentration of IL-17A.

In any of the methods of the present invention, the concentration of IL-17A in the stimulated tear sample can be determined by contacting the stimulated tear sample with an antibody that specifically binds IL-17A, and detecting antibody that has bound to the IL-17A. As an option, the antibody that specifically binds IL-17A can be a component of an immunochromatic assay.

In any of the methods of the present invention, the patient can be prescribed or provided contact lenses for the vision correction and/or the treatment for reducing discomfort associated with contact lens wear can be selected from administration of a neuropathic agent, an anti-inflammatory agent, a wetting eye drop, or any combinations thereof.

In any of the methods of the present invention, the treatment for preventing or reducing discomfort associated with contact lens wear can be or include prescribing the patient spectacle lenses for vision correction.

In any of the methods of the present invention, the prescription can be for contact lenses for the vision correction and/or for administering a neuropathic agent, an anti-inflammatory agent, a wetting eye drop, or any combinations thereof.

In any of the methods of the present invention, the prescription can be for spectacle lenses for vision correction.

The following details are applicable to the methods summarized above unless context dictates otherwise. Throughout this disclosure, a reference to "an example" or "a specific example" or similar phrase, is intended to introduce a feature or features of the method, device, etc. (depending on context) that can be combined with any combination of previously-described or subsequently-described examples (i.e. features), unless a particular combination of features is mutually exclusive, or if context indicates otherwise. As used herein, tears collected from a patient are considered "non-stimulated" if the patient's eyes have not been subjected to significant mechanical stimulus prior to collection of the tear sample. As used herein, a significant mechanical stimulus refers to a mechanical force to the eye that could potentially result in membrane deformation to activate polymodal and/or mechanoreceptors. In some examples, the patient's eyes have not been subjected to a significant mechanical stimulus for at least 30 minutes, 1 hour, 2 hour, or 4 hours prior to collection of the non-stimulated tear sample. Examples of significant mechanical stimulus include contact lens wear, exposure to windy conditions, rubbing the eyes, exposure to significant pollution, chemical exposure, and other stimuli that may activate one or more sensory neurons. In addition, conditions such as allergy and conjunctivitis may also activate polymodal receptors, and thus it is preferable to delay collection of the non-stimulated tear sample until after these conditions have cleared. In one example, the patient has not worn contact lenses for at least 12 hours, 16 hours, 24 hours, or 48 hours prior to collection of the non-stimulated tear sample.

The tear sample may be collected using any suitable method that permits measurement of IL-17A in the collected sample. In one example, the tear sample is collected by a microcapillary tube. In another example, the tear sample is collected using an absorbent strip of material. Suitable materials for collecting tear samples are known in the art (see e.g. Sia et al., Int J Opthalmol Clin Res (2016) 3:048). Conveniently, the tear collection device may be a part of a test kit used to measure IL-17A in a tear sample as described in more detail below. During collection of the tear sample, care is taken to avoid any irritation to the eye to avoid reflex tearing so that only basal tears are collected. Tears for one or both eyes may be collected. When tears from both eyes are collected, the collected tears may be pooled to make a single sample. Alternatively the IL-17A concentrations may be measured in both of the collected tear samples (i.e. the sample from the left eye, and the sample from the right eye). In one example, the first tear sample collected, which is typically the non-stimulated tear sample, is stored in a freezer until after collection of the second tear sample (typically the stimulated tear sample) so that IL-17A concentration in both tear samples may be tested at the same time. In another example, the IL-17A concentration in the first tear sample collected may be tested directly after collection, such as within 60 minutes, 30 minutes, or 10 minutes after collection.

As used herein, a "stimulated tear sample" refers to basal tears collected from a patient whose eye has been subjected to a significant mechanical stimulus prior to collection of the tear sample. Typically, both eyes will be subjected to the same mechanical stimulus. The stimulated tear sample may be collected from one of the eyes or from both of the eyes. If collected from both eyes, the tears from each eye may be pooled to make a single stimulated tear sample, or they may be individually tested for IL-17A concentration. In one example, when the tear sample from each eye is individually tested, the higher of the two IL-17A concentrations measured may be used to classify the patient as symptomatic or asymptomatic. As with the non-stimulated tear sample, care is taken to avoid reflex tearing during tear collection. In one example, contact lens wear provides the significant mechanical stimulus to the eye. In various examples, the contact lenses are worn for at least 2 hours, 4 hours, or 6 hours prior to collection of the tear sample. In some examples, the contact lens may be removed from the patient's eyes and the stimulated tear sample is collected directly from the removed contact lenses.

In some examples, when the stimulus is contact lens wear, the non-stimulated tear sample and the stimulated tear sample may be collected on different days. In such an example, the two samples may be collected at approximately the same time of the day. For example, the second sample may be collected within ±120 minutes, ±90 minutes, or ±60 minutes from the time of day the first sample was collected. In some examples, the samples are collected after the patient has been awake for about 2 to 6 hours. In another example, both the non-stimulated tear sample and the stimulated tear sample may be collected on the same day. For example, a non-stimulated tear sample may be collected from the patient, followed by subjecting the patient's eye to a significant mechanical stimulus, such as contact lens wear for at least 2, 4, or 6 hours, then collecting the stimulated tear sample.

A stimulus other than contact lens wear may be used as the mechanical stimulus for generating the stimulated tear sample provided that the stimulus results in a significant correlation between IL-17A concentrations and CLDEQ-8 scores when tested in a clinical study, such as described in Example 1 below.

The concentration of IL-17A in the tear sample(s) may be determined using any suitable method. Exemplary methods are well-known in the art including cytometric bead arrays, ELISA assays, lateral flow immunoassays such as immunochromatic assays, microfluidic (e.g. "lab on a chip") immunoassays, etc. The use of a cytometric bead array is detailed in Example 1 below. Kits for determining a predisposition for symptomatic contact lens wear are described further below. The phrase "determining a concentration of IL-17A" includes both quantitative and/or qualitative determinations. Thus, in one example, the concentration of IL-17A in a tear sample, typically in units of pg/ml, may be measured. In another example, the amount of IL-17A in a stimulated tear sample may be determined to be higher or lower than that of a baseline IL-17A concentration. In yet another example, the amount of IL-17A in a stimulated tear sample may be determined to be higher or lower than that of a cut-off value predetermined to be associated with a predisposition to symptomatic contact lens wear.

A cut-off value associated with a predisposition to symptomatic contact lens wear may be predetermined in a clinical study, such as described in Example 1 below. Variations in the general method for generating the stimulated tear sample, may determine the particular cut-off value that is selected. For example, the type of stimulus used to generate the stimulated tear sample and the duration of the stimulus, are among factors that may influence the concentration of IL-17A in the stimulated tear sample. Additionally, as is appreciated in the field of medical diagnostics, the desired specificity and sensitivity of the test will also factor into the selection of cut-off value for the method. In various examples, the cut-off value predetermined to be associated with a predisposition to symptomatic contact lens wear is at least 70, 75, 80, 85, 90, 95, 100, 105, 110, 115, 120, 125, 130, 135, 140, 145, or 150 pg/ml IL-17A. In some examples, the cut-off value predetermined to be associated with a predisposition to symptomatic contact lens wear is at least 75 pg/ml, 100 pg/ml, or 125 pg/ml, up to about 350 pg/ml, or 400 pg/ml. Throughout this disclosure, when the last value in a series of numerical values is followed by a unit of measurement, that unit of measurement is intended to implicitly follow each value in the series unless context dictates otherwise. Thus, in the above listings, the unit pg/ml is intended to follow each value listed (i.e. 70 pg/ml, 75 pg/ml, etc.).

In the method wherein the baseline concentration of IL-17A is determined in a non-stimulated tear sample of the patient, the patient may be classified as being predisposed to symptomatic contact lens wear if the concentration of IL-17A in the stimulated tear sample is higher than the baseline concentration of IL-17A. In other examples, the patient may be classified as being predisposed to symptomatic contact lens wear if the concentration of IL-17A in the stimulated tear sample is at least 125%, 150%, 175%, 200%, 225%, 250%, 275%, or 300% higher than that of the baseline concentration. Again, the amount of increase in IL-17A concentration that is selected to be a predictor of symptomatic contact lens wear may depend on the methodology used in generating the stimulated tear sample, and the degree of specificity and sensitivity desired of the method. In yet another example, the patient may be classified as being predisposed to symptomatic contact lens wear if the concentration of IL-17A in the stimulated tear sample is both 1) higher than the baseline concentration of IL-17A and 2) at or above a cut-off value associated with a predisposition to symptomatic contact lens wear.

The methods described herein advantageously enable the eye-care professional to provide better patient care and management, which may lead to higher patient satisfaction and retention. The eye-care professional may provide different aftercare scheduling or advice to a patient who is determined to be predisposed to symptomatic contact lens wear compared to a patient who is determined to be predisposed to asymptomatic contact lens wear. For example, a patient that is determined to be predisposed to symptomatic contact lens wear may be prescribed a more comfortable, premium lens and/or an eye treatment such as wetting eye drops that promote ocular comfort, anti-inflammatory agents such as corticosteroids, or other treatments that may attenuate contact lens discomfort.

As mentioned above, any conventional method, and in particular, any conventional immunoassay method, may be used to determine the concentration of IL-17A in a tear sample. Having discovered the association between IL-17A concentration in a stimulated tear sample and predisposition to symptomatic contact lens wear enables the design of immunoassay kits and devices that are specifically tailored for testing tear samples for identifying patients as being predisposed to asymptomatic or symptomatic contact lens wear.

Figure 1:
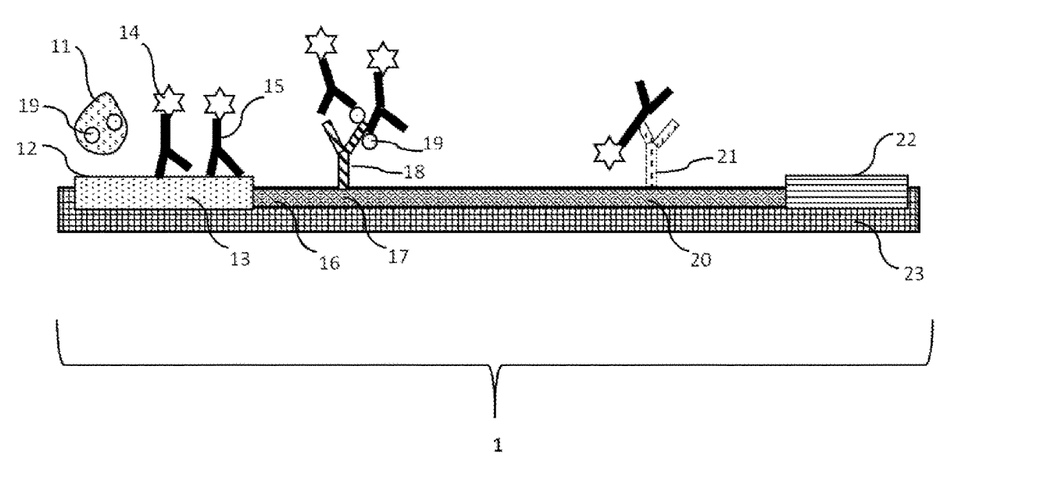
FIG. 1 depicts an exemplary immunoassay device for detection of IL-17A in a tear sample.

In one example, a kit for determining a predisposition for symptomatic contact lens wear in a patient, comprises an antibody that specifically binds to IL-17A, wherein a high risk of symptomatic contact lens wear is determined using the kit if the concentration of IL-17A in a stimulated tear sample of the patient is higher than a cut-off value predetermined to be associated with symptomatic contact lens wear. In various examples, the cut-off value is at least 70, 75, 80, 85, 90, 95, 100, 105, 110, 115, 120, 125, 130, 135, 140, 145, or 150 pg/ml IL-17A. An exemplary kit for determining a predisposition for symptomatic contact lens wear in a patient comprises a lateral flow chromatographic test strip device. Referring to FIG. 1, a tear sample, 11, is applied to a sample application zone, 12, which typically comprises an absorbent material. As depicted in FIG. 1, the sample application zone may be adjacent to and in fluid communication with a reagent zone, 13. In other examples, the sample may be applied directly to the reagent zone, i.e. the sample application zone and the reagent zone are at the same location of the test device. Both such examples are considered herein to have a sample application zone in fluid communication with a reagent zone.

In one example, reagent zone, 13, comprises an absorbent material with an antibody conjugate releasably bound thereto. The antibody conjugate comprises a detectable label, 14, conjugated to a first capture antibody, 15, that specifically binds IL-17A. As used herein, the term "antibody" includes any suitable antibody or antibody fragment (e.g. polyclonal, monoclonal, Fab, etc.). When the reagent zone is wetted by the sample, the antibody conjugate is released from the reagent zone and wicks into and through test strip, 16, which comprises test zone, 17, comprising a second capture antibody, 18, that specifically binds IL-17A, 19, present in the sample. The second capture antibody typically binds IL-17A at a different epitope than the first capture antibody. In some examples, the first capture antibody is a monoclonal antibody, and the second capture antibody is a polyclonal antibody. If a high enough concentration of IL-17A is present, label, 14, will sufficiently concentrate at test zone, 17, so that it can be detected.

After the sample and capture antibodies reach the test zone, remaining sample and antibody conjugate will continue to wick through the test strip to control zone, 20, which, in one example, may comprise a control antibody, 21, that binds to the antibody conjugate. In this example, detection of label, 14, at the control zone indicates that the test device has functioned properly. In other examples, the control zone may comprise a reagent, such as an enzyme or antibody, which reacts with a component normally present in tears to provide a signal indicating that the test has functioned properly. In some examples, the lateral flow chromatographic test strip device may also comprise an absorbent pad, 22, to absorb residual sample, and/or a liquid-impermeable backing or housing, 23.

FIG. 1, depicts the presence of IL-17A, 19, in tear sample, 11. At sufficiently high concentration of IL-17, the label will be detectable at test zone, 17. In one example, the amount of first capture antibody present in the test zone may be selected so that the label is detectable only when the concentration of IL-17A in the tear sample is equal to or greater than a cut-off value predetermined to be associated with symptomatic contact lens wear. In such example, an amount of control antibody, 21, present in control zone, 20, may be selected to capture an amount of conjugate antibody to provide a level of detectable signal representative of a cut-off value predetermined to be associated with symptomatic contact lens wear. In such example, if the concentration of label bound to the test zone is equal to or higher than the concentration of label bound to the control zone, the patient is identified as being predisposed to symptomatic contact lens wear.

A variety of detectable labels suitable for use in lateral flow chromatographic test strip devices are well known in the art. In one example, detectable label, 14, is visually detectable when sufficiently concentrated. Visually detectable labels, such as colloidal gold, are particularly convenient for testing samples in an eye care practitioner office because special equipment for label detection is not required. In other examples, the label may be an enzyme that generates a color when a substrate for the enzyme is added to the test strip. In such example, the kit may additionally comprise a reagent comprising the substrate. The reagent is applied to the test strip after the sample has been added, and the substrate is allowed to react with the enzyme label for a sufficient amount of time prior to reading the test results.

It will be appreciated that alternatives to the immunoassay device exemplified by FIG. 1 may be employed in the practice of the invention. As an alternative example, both the first capture antibody and the second capture antibody may be present in the reagent zone. IL-17A, if present in the tear sample, will form an immunocomplex with both the first and second capture antibodies. In this example, the first capture antibody may comprise a detectable label, and the test zone may comprise a molecule that specifically binds the second capture antibody. For example, the second capture antibody may be biotinylated and the test zone may comprise avidin, streptavidin, or another biotin-binding molecule. In the above described examples, and in other examples not specifically described herein, a unifying feature is the use of an antibody that specifically binds IL-17A in the manufacture of a device for the diagnosis of predisposition to symptomatic contact lens wear in a patient.

The kit for determining a predisposition for symptomatic or asymptomatic contact lens wear will typically include a tear collection device, such as a microcapillary tube or an absorbent strip of material. In some examples, the lateral flow chromatographic test strip device may be configured to receive the tear collection device at the sample application zone. Such configurations have been previously described in the art (e.g. see U.S. Pat. No. 7,723,124, see also InflammaDry®, by Quidel Corporation).

The invention also provides kits for determining a predisposition for asymptomatic contact lens wear in a patient, where predisposition for asymptomatic contact lens wear is determined using the kit if the concentration of IL-17A in a stimulated tear sample of the patient is lower than the concentration of IL-17A in a non-stimulated tear sample of the patient. In one example, the kit may comprise a device comprising two lateral flow chromatographic test strips that are parallel to each other and contained within a single housing. The non-stimulated tear sample is applied to one of the strips, and the stimulated tear sample is applied to the other strip. The housing may include a liquid-impermeable divider between the two strips to prevent cross-contamination of the samples. Each of the test strips may contain the same components as described above, e.g. a sample application zone, a test zone, and a control zone, etc. However, in this example, predisposition for asymptomatic contact lens wear is determined if the amount of label concentrated at the test zone of the test strip for the stimulated tear sample is less than that at the test zone of the test strip for the non-stimulated tear sample.

Any one or more of the above-described kits or parts thereof or components thereof can be utilized in any of the methods described herein.

The following Examples illustrate certain aspects and advantages of the present invention, which should be understood not to be limited thereby.

EXAMPLE 1

This project was conducted in accordance with the tenets of Declaration of Helsinki and was approved by the University of Melbourne Human Research Ethics Committee (Health Sciences subcommittee, HREC #1443431). All participants provided written informed consent to participate.

Purpose: To gain insight into the ocular inflammatory response, assayed using clinical and immunological techniques, in people experiencing contact lens discomfort.

Design: Prospective, cross-sectional clinical study.

Participants: This study involved 38 adult participants who were full-time, silicone-hydrogel soft contact lens wearers. Participants were categorized into groups based upon a validated contact lens dry-eye questionnaire (CLDEQ-8)[22] score (n=17 'asymptomatic', CLDEQ-8 score<9; n=21 'symptomatic', CLDEQ-8 score≥13).

Methods: Comprehensive anterior eye examinations were performed at two study visits (one with, and one without, contact lens wear), separated by a week. At Visit 1, participants attended without their contact lenses in situ, with no wear for at least 24 hours. Written informed consent was obtained, followed by the taking of: comprehensive ophthalmic and medical histories, dry eye symptom assessment (Ocular Surface Disease Index, OSDI,[38] and Symptom Assessment in Dry Eye, SANDE,[39] questionnaires) and a range of established clinical approaches. Testing included the assessment of tear osmolarity, ocular redness, tear stability, ocular surface staining, meibography, tear production and basal tear collection. Basal tear samples (~5 μL/eye)

were collected from the inferior-temporal cul de sac of participants' eyes using a glass microcapillary tube (Drummond Scientific 20 μl MicroCap), as previously described.[1] Tear flow rate was monitored to exclude dilution effects caused by reflex tearing. Only samples with a flow rate of 1 to 3 ul/min were used (i.e., any 3 ul sample collected in less than 60 seconds was excluded). Following collection, samples were centrifuged and stored at −80° C. until required for cytokine analyses. Concentrations of cytokines were assayed from basal tears using multiplex cytometric bead array. This method involves a Multiplex Cytometric Bead Array (CBA) for quantitative analysis of: IL-2, IL-4, IL-6, IL-10, IL-17A, TNF-α and IFN-γ (Human Th1/Th2/Th17 kit, BD Biosciences, San Diego, USA). Samples were acquired on a Becton Dickinson FACS Canto II flow cytometer (Franklin Lakes, NJ, USA) and data were analyzed using Becton Dickinson FCAP Array software. Changes to tear cytokine levels were measured as the percentage change from baseline, in individuals who had detectable levels of each cytokine at baseline.

Visit 2, participants wore their habitual contact lenses. To minimize any potential effects of diurnal fluctuation, visit times for Visit 2 were at approximately the same time of day (±1 hour) of Visit 1. Participants were requested to ensure several hours of contact lens wear for Visit 2 (average time period: 6.6 hours). Similar assessments were performed at both visits. In addition, at Visit 2 participants answered questionnaires to quantify the severity of lens discomfort (the validated Contact Lens Dry Eye Questionnaire-8, CLDEQ-8, and a custom-designed 'Take Home Questionnaire' (THQ), comprising of a 100 mm visual analogue scale to measure contemporaneous 'contact lens comfort' and 'contact lens dryness'). Contact lens comfort measures were recorded using the THQ at two time-points: (i) immediately upon lens application in the morning (AM), and (ii) at the study visit in the afternoon (PM).

Statistical analyses: As the inflammatory response is expected to be a common attribute between eyes, data from the right and left eyes of an individual participant were averaged to yield a single value for each parameter. Data were analyzed using GraphPad Prism 5 software package (GraphPad Software, San Diego, USA). Descriptive statistics are summarized as mean±SEM for parametric data. Data normality was assessed using the D'Agostino and Pearson omnibus test. Comparisons between groups were undertaken using the Student's t-test, analysis of variance (ANOVA) or the Mann-Whitney U test, as appropriate. A chi-squared test was used to compare discrete variables. Pairwise correlations were explored using Spearman's ($r_s$) correlation coefficients. An alpha value of 0.05 was adopted for statistical significance.

Results: At baseline, there was no significant difference in key clinical signs between asymptomatic and symptomatic contact lens wearers (p>0.05) and an absence of signs indicative of dry eye disease. People experiencing contact lens discomfort had higher levels of IL-17A (122.6±23.7 versus 44.0±10.0 pg/mL, p=0.02) and reduced tear stability (6.3±1.1 versus 10.4±1.6 seconds, p=0.03) after several hours of lens wear. Tear IL-17A levels correlated with both the I-SOD (r=0.43, p=0.01) and CLDEQ-8 score (r=0.40, p=0.01).

Conclusions: Contact lens wear discomfort occurs in people having normal tear film osmolarity and no clinical signs of dry eye disease, and is associated with higher levels of the pro-inflammatory cytokine IL-17A in the tear film. This finding provides evidence for an association between the discomfort response and low-grade, ocular surface inflammation.

REFERENCES

1. Jackson D, Zeng W, Wong C, et al. Tear interferon-gamma as a biomarker for evaporative dry eye disease. Invest Ophthalmol Vis Sci 2016; 57(11):4824-30.
2. Bullimore M A, Sinnott L T, Jones-Jordan L A. The risk of microbial keratitis with overnight corneal reshaping lenses. Optom Vis Sci 2013; 90(9):937-44.
3. Acera A, Vecino E, Duran J A. Tear MMP-9 levels as a marker of ocular surface inflammation in conjunctivochalasis. Invest Ophthalmol Vis Sci 2013; 54(13):8285-91.
4. Acera A, Rocha G, Vecino E, et al. Inflammatory markers in the tears of patients with ocular surface disease. Ophthalmic Res 2008; 40(6):315-21.
5. Validad M H, Khazaei H A, Pishjoo M, Safdari Z. The Study of Interleukin-17 Level in Vernal Keratoconjunctivitis Disease and its Relationship between Symptom and Sign Severity. Semin Ophthalmol 2016:1-4.
6. Epstein S P, Gadaria-Rathod N, Wei Y, et al. HLA-DR expression as a biomarker of inflammation for multicenter clinical trials of ocular surface disease. Exp Eye Res 2013; 111:95-104.
7. Gao J, Morgan G, Tieu D, et al. ICAM-1 expression predisposes ocular tissues to immune-based inflammation in dry eye patients and Sjogrens syndrome-like MRL/lpr mice. Exp Eye Res 2004; 78(4):823-35.
8. Jung J W, Han S J, Song M K, et al. Tear Cytokines as Biomarkers for Chronic Graft-versus-Host Disease. Biol Blood Marrow Transplant 2015; 21(12):2079-85.
9. Massingale M L, Li X, Vallabhajosyula M, et al. Analysis of inflammatory cytokines in the tears of dry eye patients. Cornea 2009; 28(9):1023-7.
10. Robciuc A, Rantamaki A H, Jauhiainen M, Holopainen J M. Lipid-modifying enzymes in human tear fluid and corneal epithelial stress response. Invest Ophthalmol Vis Sci 2014; 55(1):16-24.
11. Lanza N L, Valenzuela F, Perez V L, Galor A. The Matrix Metalloproteinase 9 Point-of-Care Test in Dry Eye. Ocul Surf 2016; 14(2):189-95.
12. Aluri H S, Kublin C L, Thotakura S, et al. Role of Matrix Metalloproteinases 2 and 9 in Lacrimal Gland Disease in Animal Models of Sjogren's Syndrome. Invest Ophthalmol Vis Sci 2015; 56(9):5218-28.
22. Chalmers R, Begley C G, Moody K, Hickson-Curran S B. Contact Lens Dry Eye Questionnaire-8 (CLDEQ-8) and opinion of contact lens performance. Optom Vis Sci 2012; 89(10):1435-42.
23. Nichols J J, Willcox M D, Bron A J, et al. The TFOS International Workshop on Contact Lens Discomfort: executive summary. Invest Ophthalmol Vis Sci 2013; 54(11):TFOS7-TFOS13.
24. Dumbleton K, Woods C A, Jones L W, Fonn D. The impact of contemporary contact lenses on contact lens discontinuation. Eye Contact Lens 2013; 39:92-8.
25. The definition and classification of dry eye disease: report of the Definition and Classification Subcommittee of the International Dry Eye WorkShop (2007). Ocul Surf 2007; 5(2):75-92.
26. Efron N. Contact lens wear is intrinsically inflammatory. Clin Exp Optom 2017; 100(1):3-19.
27. Schultz C L, Kunert K S. Interleukin-6 levels in tears of contact lens wearers. J Interferon Cytokine Res 2000; 20(3):309-10.

28. Moschos M M, Eperon S, Guex-Crosier Y. Increased eotaxin in tears of patients wearing contact lenses. Cornea 2004; 23(8):771-5.
29. Dogru M, Ward S K, Wakamatsu T, et al. The effects of 2 week senofilcon-A silicone hydrogel contact lens daily wear on tear functions and ocular surface health status. Cont Lens Anterior Eye 2011; 34(2):77-82.
30. Poyraz C, Irkec M, Mocan M C. Elevated tear interleukin-6 and interleukin-8 levels associated with silicone hydrogel and conventional hydrogel contact lens wear. Eye Contact Lens 2012; 38(3):146-9.
31. Thakur A, Willcox M D. Contact lens wear alters the production of certain inflammatory mediators in tears. Exp Eye Res 2000; 70(3):255-9.
32. Willcox M D, Zhao Z, Naduvilath T, Lazon de la Jara P. Cytokine changes in tears and relationship to contact lens discomfort. Mol Vis 2015; 21:293-305.
33. Lopez-de la Rosa A, Martin-Montanez V, Lopez-Miguel A, et al. Corneal Sensitivity and Inflammatory Biomarkers in Contact Lens Discomfort. Optom Vis Sci 2016; 93(8):892-900.
34. Willcox M D. Is There a Role for Inflammation in Contact Lens Discomfort? Eye Contact Lens 2017; 43(1):5-16.
35. Levi-Montalcini R, Skaper S D, Dal Toso R, et al. Nerve growth factor: from neurotrophin to neurokine. Trends Neurosci 1996; 19(11):514-20.
36. Masoudi S, Stapleton F J, Willcox M D. Contact Lens-Induced Discomfort and Protein Changes in Tears. Optom Vis Sci 2016; 93(8):955-62.
37. Liu Q, McDermott A M, Miller W L. Elevated nerve growth factor in dry eye associated with established contact lens wear. Eye Contact Lens 2009; 35(5):232-7.
38. Schiffman R M, Christianson M D, Jacobsen G, et al. Reliability and validity of the Ocular Surface Disease Index. Arch Ophthalmol 2000; 118(5):615-21.
39. Schaumberg D A, Gulati A, Mathers W D, et al. Development and validation of a short global dry eye symptom index. Ocul Surf 2007; 5(1):50-7.

What is claimed is:

1. A kit for determining a predisposition for symptomatic contact lens wear in a patient, said kit comprising an antibody that specifically binds to IL-17A, wherein a high risk of symptomatic contact lens wear is determined using the kit if the concentration of IL-17A in a stimulated tear sample of the patient is higher than a cut-off value predetermined to be associated with symptomatic contact lens wear and wherein said kit further comprising a lateral flow chromatographic test strip that comprises a sample application zone; a reagent zone comprising an antibody conjugate comprising a detectable label conjugated to a first capture antibody that specifically binds IL-17A, wherein the antibody conjugate is in fluid communication with the sample application zone; and a test zone comprising a second capture antibody that specifically binds IL-17A in fluid communication with the reagent zone.

2. The kit of claim 1, wherein the cut-off value is at least 75 pg/ml.

3. A kit for determining a predisposition for asymptomatic contact lens wear in a patient, said kit comprising an antibody that specifically binds to IL-17A, wherein a predisposition for asymptomatic contact lens wear is determined using the kit if the concentration of IL-17A in a stimulated tear sample of the patient is lower than the concentration of IL-17A in a non-stimulated tear sample of the patient and further comprising a lateral flow chromatographic test strip comprising:
   a) a first sample application zone for applying the non-stimulated tear sample;
   b) a second sample application zone for applying the stimulated tear sample;
   c) a first reagent zone in fluid communication with the first sample application zone,
   d) a second reagent zone in fluid communication with the second sample application zone,
   e) a first test zone in fluid communication with the first reagent zone, and
   f) a second test zone in fluid communication with the second reagent zone,
   wherein the first and second reagent zones each comprise an antibody conjugate comprising a detectable label conjugated to a first capture antibody that specifically binds IL-17A, the first and second test zones each comprise a second capture antibody that specifically binds IL-17A, and wherein a lower concentration of IL-17A in the stimulated tear sample of the patient is determined by a lower concentration of the detectable label in the first reagent zone compared to the second reagent zone after application of the non-stimulated and stimulated tear samples to the first and second sample application zones, respectively.

4. The kit of claim 1, further comprising a tear collection device.

* * * * *

UNITED STATES PATENT AND TRADEMARK OFFICE
CERTIFICATE OF CORRECTION

PATENT NO. : 12,124,113 B2
APPLICATION NO. : 18/114287
DATED : October 22, 2024
INVENTOR(S) : Downie et al.

Page 1 of 1

It is certified that error appears in the above-identified patent and that said Letters Patent is hereby corrected as shown below:

On the Title Page

Item (73) Assignee:
"COOPERVISION INTERNATIONAL LIMITED, Fareham (GB)" should read -- COOPERVISION INTERNATIONAL LIMITED, Fareham (GB) and THE UNIVERSITY OF MELBOURNE, Victoria (AU) --

Signed and Sealed this
Thirty-first Day of December, 2024

Derrick Brent
*Acting Director of the United States Patent and Trademark Office*